(12) United States Patent
Böhner et al.

(10) Patent No.: US 8,106,109 B2
(45) Date of Patent: Jan. 31, 2012

(54) DENTAL FILLING MATERIAL

(75) Inventors: Ralf Böhner, Kriessern (CH); Dierk Lübbers, Halstenbek (DE); Silvan Benz, Oberriet (CH)

(73) Assignee: Coltene Whaledent AG, Altstatten (CH)

( * ) Notice: Subject to any disclaimer, the term of this patent is extended or adjusted under 35 U.S.C. 154(b) by 560 days.

(21) Appl. No.: 12/118,867

(22) Filed: May 12, 2008

(65) Prior Publication Data

US 2009/0023115 A1    Jan. 22, 2009

Related U.S. Application Data

(60) Provisional application No. 60/950,927, filed on Jul. 20, 2007.

(51) Int. Cl.
*A61K 6/06* (2006.01)
*A61K 6/08* (2006.01)
*A61K 6/083* (2006.01)
*C08F 2/50* (2006.01)
*C08J 3/28* (2006.01)
*A61K 6/02* (2006.01)

(52) U.S. Cl. ........ 523/116; 523/105; 523/109; 523/113; 523/114; 523/115; 523/117; 523/120; 523/300; 522/77; 522/79; 522/81; 522/82; 522/83; 522/84; 522/86; 522/178; 522/182; 522/908; 106/35

(58) Field of Classification Search ............. 522/74, 522/77, 79, 81, 82, 83, 84, 86, 178, 182, 522/908; 523/105, 109, 113, 114, 115, 116, 523/117, 120, 300; 106/35
See application file for complete search history.

(56) References Cited

U.S. PATENT DOCUMENTS

| | | | |
|---|---|---|---|
| 5,130,347 A | 7/1992 | Mitra | |
| 6,284,030 B1 * | 9/2001 | Orlowski et al. | 106/35 |
| 2002/0045678 A1 * | 4/2002 | Lopez et al. | 523/116 |

OTHER PUBLICATIONS

Sfondrini et al. Halogen versus high-intensity light-curing of uncoated and pre-coated brackets: a shear bond strength study. Journal of Orthodontics, vol. 29, Mar. 2002, pp. 45-50.*

"Radiation Curing", Kirk-Othmer Encyclopedia for Chemical Technology. 3rd Edition, vol. 19, pp. 607-625, 1982.

* cited by examiner

*Primary Examiner* — Sanza McClendon
(74) *Attorney, Agent, or Firm* — Katten Muchin Rosenman LLP

(57) ABSTRACT

The invention concerns a dental filling material with dual hardening mechanism, wherein i) a first hardening mechanism is based on a photocuring reaction, preferably a radical reaction, and ii) a second hardening mechanism is dependent on $H_2O$ as a reactant, especially as a ligand. Preferably, the second hardening mechanism is a gypsum-type reaction. Owing to the expansion of the composition an excellent marginal seal can be achieved, while the first hardening mechanism allows for a rapid cure on demand.

22 Claims, No Drawings

DENTAL FILLING MATERIAL

The present invention relates to dental filling materials, especially dental filling materials for use in intermediate restoration of tooth cavities and root canals.

The following materials are most commonly used for temporary dental restoration: (i) zinc phosphate cements; (ii) silicate cements such as glass ionomer cements (GIC); (iii) zinc oxide eugenol cements; (iv) gutta-percha; (v) gypsum-type cements (such as e.g. CAVIT®, 3M Espe, DE-Seefeld and Coltosol®, Coltène Whaledent, CH-Altstätten); (vi) composite materials (e.g. Fermit, Ivoclar Vivadent)

GICs (vide supra, ii)) are known since 1972. The general concept of GICs is the reaction of an aqueous polyalkenoic acid such as e.g. a polyacrylic acid and a solid glass component that is usually a fluoroaluminosilicate. An acid/base reaction occurs and the metallic polyalkenoate salt precipitates until the GIC is hardened. The typical setting and working time of GICs is about two minutes. Moreover, dual-cured GICs are known which allow for a cure on demand by subjecting the material to radiant energy before the end of the otherwise resulting working time due to conventional setting of the GIC; cf U.S. Pat. No. 5,130,347. Though the GICs only slightly shrink upon curing, the shrinkage of such materials may hamper the marginal seal of the restoration; it is currently controversially discussed whether the polymerization shrinkage is significant enough to disrupt the marginal seal. In any case, already the risk of a disrupted marginal seal is not tolerable.

Gypsum type cements are cheap and easy to apply. They do not require mixing, because they cure with the humidity in the mouth.

The drawback of gypsum-type cements is that the curing takes about 1 hour until the filling can be loaded to a reasonable extend.

Composite type cements shrink and therefore do not show a sufficient sealing of the cavity due to leakage.

It is thus an object of the present invention to overcome the above mentioned drawbacks of the prior art, especially to provide a dental filling material which allows for a reliable marginal seal and an at least partial cure on demand.

This object is solved inter alia by a dental filling material with dual hardening mechanism, wherein
i) a first hardening mechanism is based on a photocuring reaction, preferably a radical reaction, and
ii) a second hardening mechanism is dependent on $H_2O$ as a reactant (especially as a ligand); a gypsum-type reaction is preferred.

In the first hardening mechanism, photocuring of the dental filling material can be performed by exposure to an appropriate source of radiant energy, depending on the photocurable reactants within the dental filling material. This may lead to a curing at least on the surface layer of the material (approx. 1 mm deep).

Preferably, the photocurable reactants of the filling material are resins possessing an organic backbone and a photocurable group chosen from the group consisting of ethylenically unsaturated groups that are polymerizable in a free radical mechanism, such as e.g. acrylates, methacrylates, alkenes, acrylamides and combinations thereof.

The dental filling material is preferably configured such as to allow for the first hardening mechanism being initiated by radiant energy in the ultra-violet or, preferred, visible light range. Towards this end, suitable inducer molecules that act as a source of free radicals when activated can be incorporated into the dental filling material.

Examples of suitable ultraviolet-induced polymerization initiators include, but are not limited to, ketones such as benzyl and benzoin, acyloins and acyloin ethers, commercially available e.g. from Sigma Aldrich.

Examples of suitable visible-light-induced initiators include, but are not limited to, suitable combinations of a diketone, e.g. camphorquinone, a diaryliodonim salt, e.g. diphenyliodonium chloride, -bromide, -iodide or hexafluorophosphate, with or without additional hydrogen donors, or accelerators, such as sodium benzene sulfinate, amines or amine alcohols. A currently preferred visible-light initiator is the combination of camphorquinone (or other type II photoinitiator(s)) and 2-ethylhexyl-p-dimethylaminobenzoate as an effective amine synergist.

Preferably, the photocuring reaction is susceptible to initiation by irradiation with visible light, especially with blue light, preferably light of a wavelength in the range of about 400 nm to about 500 nm, most preferably of about 420 nm to about 480 nm. The radiation curing as such is well know in the art; it is referred to "Radiation Curing", Kirk-Othmer Encyclopedia or Chemical Technology, $3^{rd}$ Ed., Vol. 19, pp 607-624 (1982), incorporated herein by reference, with respect to suitable radiant energy sources and desired combinations of such properties as safety, controllability, suitable intensity and suitable distribution of incident energy.

In the second hardening mechanism, $H_2O$ acts as a reactant, especially as a ligand. Thus, $H_2O$ not only indirectly serves as a carrier medium for molecules, especially ions, that are to react with each other, as it is the case with GICs. In contrast, water in fact acts as a reactant itself in the second hardening mechanism, i.e. water becomes chemically incorporated into the dental filling material, e.g. as a ligand. Most preferably, the second hardening mechanism comprises is a gypsum-type reaction; this may comprise the addition of crystal water. Typical, and currently preferred, reactions of the second hardening mechanism are, either alone or in combination:

i) the addition of crystal water to water deficient $CaSO_4$, preferably $CaSO_4$ with $\leq\frac{1}{2}$ molecules of crystal water, most preferably $CaSO_4 \cdot \frac{1}{2} H_2O$:

The re-hydration of especially $CaSO_4 \cdot \frac{1}{2} H_2O$ (calcium sulphate hemihydrate) to $CaSO_4 \cdot 2 H_2O$ is commonly known as the gypsum reaction in the dental technique. According to EN ISO 6873 dental gypsum can be classified as follows:

Type I (impression gypsum, β-hemihydrate);
Type II (alabaster gypsum, β-hemihydrate);
Type III (hard gypsum, α-hemihydrate);
Type IV (super hard gypsum with low expansion, α-hemihydrate);
Type V (super hard gypsum with high expansion, α-hemihydrate);

in the context of the present invention, all types of gypsum according to EN ISO 6873 can generally be incorporated into the dental filling composition.

ii) the reaction of zinc sulphate monohydrate with zinc oxide: $ZnSO_4 \cdot H_2O + ZnO \rightarrow Zn_2(OH)_2SO_4$ and/or $ZnSO_4 + ZnO + H_2O \rightarrow Zn_2(OH)_2SO_4$, respectively.

The presence of Zn containing compounds in the dental filling materials according to the present invention is especially preferred since they synergistically serve a dual purpose: on the one hand, they harden the composition upon reaction with water according to a second hardening mechanism as outlined above; on the other hand, the antibacterial activity of Zn compounds aids in achieving a more reliable and durable restoration.

According to especially advantageous embodiments of the present invention, the dental filling material comprises:
a) about 0.1 to about 80 percent, preferably about 15 to about 50 percent by weight of ZnO, and about 0.1 to about 25 percent, preferably about 5 to about 20 percent by weight of $ZnSO_4.H_2O$ and/or $ZnSO_4$; and/or
b) about 0.1 to about 80 percent, preferably about 10 to about 60 percent by weight of $CaSO_4.\frac{1}{2} H_2O$;
about 0.001 to about 3 percent, preferably about 0.01 to about 0.5 percent by weight of a photoinitiator;
optionally, up to about 80 percent, preferably about 0.1 to about 50 percent by weight of filling material which is not sensitive to moisture.

Suitable filling materials that are not sensitive to moisture are e.g. $SiO_2$, quarz, dental glasses, polyethylene powder, pyrogenic silica.

As is known in the art, suitable premature polymerization inhibitors such as, but not limited to, butylated hydroxytoluene (BHT) may advantageously be incorporated into the dental filling composition, which may prevent premature curing of such free radical polymerizable compositions.

For the sake of clarity, the dental filling material is now further described in the context of yet another aspect the present invention, i.e. a method of restoration of a dental cavity or root canal, comprising the steps of
i) applying a dental filling material as outlined above into a dental cavity or root canal;
ii) initiating the hardening of the surface layer of the dental filling material by a first hardening mechanism as outlined above;
iii) allowing the dental filling material below the said surface layer to at least partially set by a second hardening mechanism as outlined above.

It is a general advantage of the above mentioned gypsum-type reactions, especially the additions of crystal water to water deficient $CaSO_4$ or $ZnSO_4$, that the shrinkage due to the hardening is compensated by the water uptake of the gypsum reaction. Thereby, the marginal seal of the dental cavity is known to be very good. However, the expansion of the dental composition material due to the second hardening mechanism inside the cavity is found, according to the present invention, compatible with the pre-formed, hardened surface layer of the filling material, formed by the first hardening mechanism. This is quite surprising since one might have had expected that further expansion under a pre-formed, hardened surface might again result in breaking up of the marginal seal of the surface layer, which is however not the case. Most important, shrinkage due to the polymerisation is compensated by the water uptake of the gypsum, thus providing a very good marginal seal, while in parallel also providing for the beneficial effect of on-demand curing of a surface layer (as is known from the dual-cured GICs, which however tend to shrink upon curing). Compared to the GICs, the present invention provides compositions that do not require any mixing, i.e. are one-component compositions, and which are cheap. In view of composite type cements, the shrinkage upon cure is much lower, thereby the sealing is enhanced.

Yet another aspect of the present invention concerns a method of manufacturing of a material as outlined above, wherein at least
about 1 to about 40 percent, preferably about 5 to about 30 percent by weight of at least one photocurable resin as outlined above;
a) about 0.1 to about 80 percent, preferably about 15 to about 50 percent by weight of ZnO, and about 0.1 to about 25 percent, preferably about 5 to about 20 percent by weight of $ZnSO_4.H_2O$ and/or $ZnSO_4$; and/or
b) about 0.1 to about 80 percent, preferably about 10 to about 60 percent by weight of $CaSO_4.\frac{1}{2} H_2O$;
about 0.001 to about 3 percent, preferably about 0.01 to about 0.5 percent by weight of a photoinitiator;
optionally, up to about 80 percent, preferably about 0.1 to about 50 percent by weight of filling material which is not sensitive to moisture, as outlined above,
are admixed. Mixing can e.g. carried out in a linden kneader, preferably at slightly increased temperature (e.g. 30 minutes at 50° C.)

Yet a further aspect of the present invention concerns a method of restoration of a dental cavity or root canal, comprising the steps of
i) applying a dental filling material as described above into a dental cavity or root canal;
ii) initiating the hardening of the surface layer of the dental filling material by a first hardening mechanism;
iii) allowing the dental filling material below the said surface layer to at least partially set by a second hardening mechanism, as set out above.

According to preferred embodiments, initiation of the hardening in step ii) is performed with light, especially with light of a wavelength in the range of about 400 nm to about 500 nm, preferably in the range of about 420 nm to about 480 nm.

In yet further preferred embodiments the opacity of the dental filling material is chosen such as to allow for a selective hardening of only about 1 mm of the surface layer by irradiation with a light source of dental curing lights based on LED or halogen light technology, typically in the range of about 440 to about 480 nm.

The invention will henceforth be described by way of a currently preferred embodiment, without intending to limit the inventive concept to this embodiment.

The following components are admixed in a linden kneader for 30 minutes at 50° C.:

| | |
|---|---|
| 30.00 weight percent | ZnO (Grillo-Werke AG, "Zinkweiss Pharma A"); |
| 13.00 weight percent | $ZnSO_4 \cdot H_2O$ (Grillo-Werke AG, "Zinksulfatmonohydrat USP"); |
| 40.00 weight percent | Dental gypsum (Heboroc; BPB Formula); |
| 17.00 weight percent | Urethanedimethacrylate, UDMA (Plex 6661-O, Degussa Röhm); |
| 00.10 weight percent | Camphorquinone; |
| 00.17 weight percent | 2-Ethylhexyl-p-dimethylaminobenzoate; |
| 00.02 weight percent | butylated hydroxytoluene, BHT |

The composition was filled into a dental cavity and a surface layer of the composition was irradiated with blue light. While the surface layer thereby got mechanically resilient, the underlying material in the cavity hardens more slowly. Owing to the expansion of the composition, the marginal seal is excellent. Moreover, the composition is bactericidal.

The invention claimed is:
1. Dental filling material with dual hardening mechanism, wherein
i) a first hardening mechanism is based on a photocuring reaction, and
ii) a second hardening mechanism is dependent on $H_2O$ as a reactant becoming chemically incorporated into the dental filling material as a ligand, and wherein the second hardening mechanism comprises
i) the hydration of water deficient $CaSO_4$; or
ii) the reaction $ZnSO_4.H_2O+ZnO \rightarrow Zn_2(OH)_2SO_4$ and/or $ZnSO_4+ZnO+H_2O \rightarrow Zn_2(OH)_2SO_4$;
or combinations thereof.

2. Dental filling material according to claim 1, wherein the photocuring reaction is susceptible to initiation by irradiation of blue light of a wavelength in the range of about 400 nm to about 500 nm.

3. Dental filling material according to claim 1, comprising acrylate and/or methacrylate resin(s), which are hardenable by photocuring.

4. Dental filling material according to claim 1, further comprising a photoinitiator.

5. Dental filling material according to claim 1, comprising:
  a) about 0.1 to about 80 percent by weight of ZnO, and about 0.1 to about 25 percent by weight of $ZnSO_4.H_2O$ and/or $ZnSO_4$; and/or
  b) about 0.1 to about 80 percent by weight of $CaSO_4.\frac{1}{2} H_2O$;
  about 0.001 to about 3 percent by weight of a photoinitiator;
  optionally, up to about 80 percent by weight of filling material which is not sensitive to moisture.

6. A method of at least partially hardening a material according to claim 1, comprising the step of irradiating the said material with blue light of a wavelength in the range of about 400 nm to about 500 nm.

7. A method of manufacturing of a material according to claim 1, wherein at least
  about 1 to about 40 percent by weight of at least one photocurable resin;
  a) about 0.1 to about 80 percent by weight of ZnO and about 0.1 to about 25 percent by weight of $ZnSO_4.H_2O$ and/or $ZnSO_4$; and/or
  b) about 0.1 to about 80 percent by weight of $CaSO_4.\frac{1}{2} H_2O$;
  about 0.001 to about 3 percent by weight of a photoinitiator;
  optionally, up to about 80 percent by weight of filling material which is not sensitive to moisture;
  are admixed.

8. A method of restoration of a dental cavity or root canal, comprising the steps of
  i) applying a dental filling material according to claim 1 into a dental cavity or root canal;
  ii) initiating the hardening of the surface layer of the dental filling material by a first hardening mechanism;
  iii) allowing the dental filling material below the said surface layer to at least partially set by a second hardening mechanism.

9. A method according to claim 8, wherein initiation of the hardening in step ii) is performed with light of a wavelength in the range of about 400 nm to about 500 nm.

10. A method according to claim 8, wherein the opacity of the dental filling material is chosen such as to allow for a selective hardening of about 1 mm of the surface layer by irradiation with an intensity of at least 300 $mW/cm^2$ at a wavelength in the range of about 440-480 nm.

11. Dental filling material with dual hardening mechanism, wherein
  i) a first hardening mechanism is based on a photocuring reaction and
  ii) a second hardening mechanism is dependent on $H_2O$ as a reactant becoming chemically incorporated into the dental filling material as a ligand.

12. Dental filling material according to claim 11, wherein the second hardening mechanism comprises hydration.

13. Dental filling material according to claim 5, wherein the dental filing material comprises about 15 to about 50 percent by weight of ZnO.

14. Dental filling material according to claim 5, wherein the dental filing material comprises about 15 to about 40 percent by weight of at least one photocurable resin.

15. Dental filling material according to claim 5, wherein the dental filing material comprises about 10 to about 60 percent by weight of $CaSO_4.\frac{1}{2} H_2O$.

16. Dental filling material according to claim 5, wherein the dental filing material comprises about 0.01 to about 0.5 percent by weight of a photoinitiator.

17. Dental filling material according to claim 5, wherein the dental filing material comprises about 0.1 to about 50 percent by weight of filling material which is not sensitive to moisture.

18. A method according to claim 7, wherein about 15 to about 50 percent by weight of ZnO are admixed.

19. A method according to claim 7, wherein about 15 to about 40 percent by weight of at least one photocurable resin are admixed.

20. A method according to claim 7, wherein about 10 to about 60 percent by weight of $CaSO_4.\frac{1}{2} H_2O$ are admixed.

21. A method according to claim 7, wherein about 0.01 to about 0.5 percent by weight of a photoinitiator are admixed.

22. A method according to claim 7, wherein about 0.1 to about 50 percent by weight of filling material which is not sensitive to moisture are admixed.

\* \* \* \* \*